(12) United States Patent
Yoon et al.

(10) Patent No.: US 6,352,718 B1
(45) Date of Patent: Mar. 5, 2002

(54) VASOPRESSIN ANTAGONIST FORMULATION AND PROCESS

(75) Inventors: Joseph K. Yoon, Palisade Park, NJ (US); Richard W. Saunders, Palisades, NY (US); Mahdi Fawzi, Morristown, NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/668,883

(22) Filed: Sep. 25, 2000

Related U.S. Application Data
(60) Provisional application No. 60/228,812, filed on Sep. 27, 1999.

(51) Int. Cl.[7] .................................................. A61K 9/64
(52) U.S. Cl. ...................... 424/456; 424/484; 424/486; 514/220; 514/561; 514/562; 514/563; 514/564
(58) Field of Search .............................. 514/220, 561, 514/562, 563, 564; 424/451, 452, 456, 484, 486

(56) References Cited

U.S. PATENT DOCUMENTS

| | | |
|---|---|---|
| 4,578,391 A | 3/1986 | Kawata et al. |
| 4,620,974 A | 11/1986 | Hersh et al. |
| 4,744,988 A | 5/1988 | Brox |
| 5,516,774 A | 5/1996 | Albright et al. |
| 5,641,512 A | 6/1997 | Cimiluca |

FOREIGN PATENT DOCUMENTS

| | | | |
|---|---|---|---|
| EP | 0815854 | | 1/1998 |
| WO | 9519579 | | 7/1995 |
| WO | 9640071 | | 12/1996 |
| WO | 9641622 | | 12/1996 |
| WO | 9936060 | | 7/1999 |
| WO | WO 2001022495 | * | 4/2001 |

OTHER PUBLICATIONS

Shah et al., Bull. Tech/Gattefosse Rep., 1996, 89, 27–28.

* cited by examiner

Primary Examiner—Thurman K. Page
Assistant Examiner—Liliana Di Nola-Baron
(74) Attorney, Agent, or Firm—Steven R. Eck

(57) ABSTRACT

This invention provides novel formulations for N-[4-(5H-pyrrolo[2,1-c][1,4]benzodiazepin-10(11H)ylcarbonyl)-3-chlorophenyl]-5-fluoro-2-methyl-benzamide, or a pharmaceutically acceptable salt thereof, and processes for making them, the formulations comprising from about 1% to about 20% of active ingredient, from about 1% to about 18% of a surfactant component, from about 50% to about 80% of a component of one or more polyethylene glycols, from about 1% to about 20% of a component of one or more sucrose fatty acid esters and/or polyvinylpyrrolidone and, optionally, one or more pharmaceutically acceptable preservatives or antioxidants

19 Claims, No Drawings

VASOPRESSIN ANTAGONIST FORMULATION AND PROCESS

This application claims the benefit of U.S. Provisional Application No. 60/228812, which was converted from U.S. patent application Ser. No. 09/405,772, filed Sep. 27, 1999, pursuant to a petition filed under 37 C.F.R. 1.53(c)(2)(i).

This applications concerns new formulations for N-[4-(5H-pyrrolo[2,1-c][1,4]benzodiazepin-10(11H)ylcarbonyl)-3-chlorophenyl]-5-fluoro-2-methylbenzamide, and pharmaceutically acceptable salts thereof, as well as processes for manufacturing the formulations. The invention particularly relates to orally administered formulations of these compounds.

BACKGROUND OF THE INVENTION

The art describes many methods of producing liquid or semi-solid encapsulated pharmaceutical formulations. In Bull. Tech./Gattefosse Rep. (1996), 89, 27–38, authors Shah et al. describe hard gelatin capsule technology, particularly for use in enhancing the bioavailability of poorly soluble or poorly absorbed drugs.

U.S. Pat. No. 4,620,974 (Hersh et al.) teaches a hard gelatin capsule comprising a telescoping two-piece cap with a lubricant comprising a polyethylene glycol of a molecular weight between about 200 and about 900 present in admixture with the composition at a concentration of from about 0.5 to about 25 weight percent.

WO 96/40071 (Lamberti) discloses methods and devices for producing minimal volume capsules. WO 96/41622 (Tanner et al.) teaches suspensions suitable for encapsulation in gelatin capsules, particularly including a solid phase of solid particles and a liquid phase capable of suspending the solid phase.

U.S. Pat. No. 5,641,512 (Cimiluca) teaches soft gelatin encapsulated analgesics in which the shell contains a xanthine derivative, such as caffeine.

U.S. Pat. No. 4,578,391 (Kawata et al.) describes oily compositions for antitumor agents comprising at least one sparingly oil soluble or water-soluble antitumor drug, at least one fat or oil, and at least one solubilizing adjuvant in an oily vehicle, selected from crown ether, lecithin, polyethylene glycol, propylene glycol, vitamin E, polyoxyehtylene alkylether, and sucrose esters of fatty acids.

EP 0 815 854 A1 discloses a substantially translucent, semi-solid fill material for a soft gelatin capsule, the semi-solid material being sufficiently viscous that it cannot be expelled from the capsule with a syringe at room temperature.

U.S. Pat. No. 4,744,988 (Brox) teaches soft gelatin capsules comprising a shell of gelatin, a softener and a filling of a polyethylene glycol and a low polyhydric alcohol and at least one active substance, characterized in that the shell contains 4 to 40 percent sorbital or sorbitanes, at least half of the weight of polyethylene glycol used is a polyethylene glycol having a mean molecular weight of 600, and the capsule filling comprises up to 20% by weight of glycerol and/or 1,2-propylene glycol.

WO 95/19579 (Dhabhar) teaches a process for solubilizing difficulty soluble pharmaceutical agents in a mixture of polyethylene glycol and propylene glycol by using a polyvinylpyrrolidone with a specific viscosity average molecular weight of from about 5,000 to about 25,000.

SUMMARY OF THE INVENTION

This invention provides orally administerable formulations for N-[4-(5H-pyrrolo[2,1-c][1,4]benzodiazepin-10(11H)ylcarbonyl)-3-chlorophenyl]-5-fluoro-2-methylbenzamide, also known as VPA-985, or the pharmaceutically acceptable salts thereof, which has the structure:

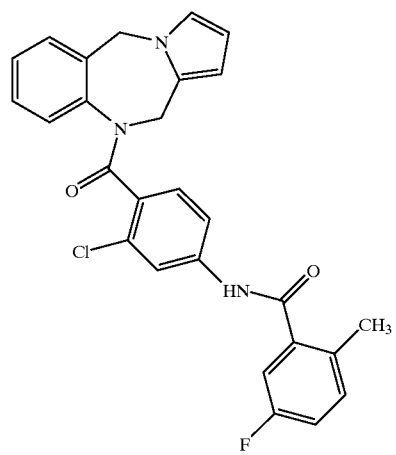

VPA-985 is a V2 receptor antagonist (vasopressin antagonist) with the ability to elicit the removal of water in mammals, without the excretion of necessary electrolytes. The synthesis of this compound and its salts is disclosed in U.S. Pat. No. 5,516,774 (Albright et al.), which is fully incorporated herein by reference. VPA-985 can be seen as Example 482 in U.S. Pat. No. 5,516,774. This compound is highly insoluble in both conventional, orally acceptable oils, such as safflower or sesame seed oils, and in aqueous systems. Therefore, its pharmaceutical formulation requires a novel approach.

The formulations of this invention comprise (by % w/w):
a) from about 1% to about 20% of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof, preferably from about 5% to about 16% of this active ingredient;
b) from about 1% to about 18% of a surfactant component, preferably from about 5% to about 10% of the surfactant component;
c) from about 50% to about 80% of a component of one or more polyethylene glycols (PEG), preferably from about 55% to about 70% of one or more different molecular weight grades of polyethylene glycols; and
d) from about 1% to about 20%, preferably from about 5% to about 15% and more preferably between about 8% and about 12%, of a component of:
  i) one or more sucrose fatty acid esters; or
  ii) a polyvinylpyrrolidone (PVP) with a K value between about 15 and 90, preferably with a K value of from about 17 as defined in USP/NF; or
  iii) a combination of one or more sucrose fatty acid esters and a PVP, as defined above.

The polyethylene glycol component may be comprised of one or more PEG polymers, preferably commercially available PEG polymers between PEG 200 and PEG 4,000, i.e. those PEG polymers having an average molecular weight between about 190 and about 4800. More preferred are PEG polymers between average molecular weights of from about 190 to about 3450, most preferably between about 400 and 1540. Among the preferred PEG polymers are PEG 400, having an average molecular weight between about 380 and about 420, and PEG 1,000, having an average molecular weight between about 950 and about 1050. The ratio of high and low molecular weight PEG species within the PEG component is preferably from about 2.5:1 to about 1:2.5, more preferably about 1:1. As an example, a preferred blend of PEG polymers within this invention would include a 1:1 blend of PEG 400 and PEG 1000. It may be preferable to choose a mixture of PEG components which will have a melting point at or near the physiological temperature of the mammal to receive the formulation. Mixtures of final components which have a viscosity range of from about 140 to about 1500 centipoise at 37° C. may be preferred, more preferably a range of from 300 to about 800 centipoise at 37° C.

The surfactants that may be used with the present formulations include, but not limited to, polysorbate 20 (polyoxyethylene 20 sorbitan monolaurate), Polysorbate 60, Polysorbate 40, polysorbate 80, Span 80 Sorbitan Oleate, a product of ICI Americas, Wilmington, Delaware, polysorbate 81, polysorbate 85, polysorbate 120, bile acids and their salts defined by Martindale The Extra Pharmacopoeia Thirtieth Edition on page 1341–1342 such as Sodium taurocholates, Sodium deoxytaurocholates, Chenodeoxycholic acid, and ursodeoxycholic acid, and pluronic or poloxamers such as Pluronic F68, Pluronic L44, Pluronic L101, or combinations of one or more of the above. Polysorbate 80, by itself or in combination with one or more other surfactants, is preferred for use with this invention.

The sucrose fatty acid esters useful with this invention include those commercially available and art recognized esters useful for orally administered pharmaceutical compositions, including monoesters, diesters and triesters of sucrose, or mixtures or blends thereof. Specific examples of esters useful with this invention are sucrose monolaurate, sucrose monomyristate, sucrose monopalminate, sucrose monostearate, sucrose distearate, sucrose tristearate, sucrose trimyristate, and sucrose tripalmitate, or combinations thereof.

In addition to these components, other enhancing or protective pharmaceutically acceptable antioxidants or preservatives may be added to the compositions of this invention to comprise up to about 4% of the composition, by weight, more preferably up to about 3%. Examples may include ascorbyl palmitate, benzyl alcohol, butylated hydroxyanisole (BHA), butylated hydroxytoluene (BHT), etc. Examples of these components in the present formulations would include BHA at a concentration from about 0.3% to about 2.5% (% w/w) and BHT at a concentration from about 0.005% to about 0.15% (% w/w), preferably with a mixture of BHA and BHT within these ranges.

A formulation of this invention utilizing one or more of these antioxidants or preservatives comprises:

a) from about 1% to about 20% of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof, preferably from about 5% to about 16% of this active ingredient;

b) from about 1% to about 18% of a surfactant component, preferably from about 5% to about 15% of the surfactant component, more preferably from about 8 to about 12% of the surfactant component;

c) from about 50% to about 80% of a component of one or more different molecular weight grades of polyethylene glycols (PEG), preferably from about 55% to about 70% of one or more polyethylene glycols;

d) from about 1% to about 20%, preferably about 5% to about 15%, of one or more sucrose fatty acid esters or polyvinylpyrrolidone (PVP) with a K value between about 15 and 90, preferably with a K value of from about 17 as defined in USP/NF; and e) from about 0.1% to about 4%, preferably from about 0.1 to about 3%, of one or more preservatives or antioxidants, for example from about 0.3% to about 2.5% (% w/w) BHA and/or from about 0.005% to about 0.15% (% w/w) BHT.

One preferred embodiment of this invention provides a pharmaceutical formulation comprising:

a) from about 5% to about 16% of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof;

b) from about 5% to about 10% of a surfactant component;

c) a component of from about 55% to about 70% of one or more different molecular weight grades of polyethylene glycols;

d) from about 5% to about 15% of polyvinylpyrrolidone (PVP) with a K value between about 15 and 90, preferably with a K value of from about 17 as defined in USP/NF; and e) from about 0.3% to about 2.5% (% w/w) BHA and from about 0.005% to about 0.15% (% w/w) BHT.

Preferably, the formulations of this invention are enclosed in a sealed enclosure after manufacture, such as soft or hard gelatin capsules. The formulations of this invention may be created as a liquid or semi-liquid formulation and introduced into a capsule. Similarly, using an acceptable range of components and/or temperatures, the formulation may be made as a gel or solid prior to encapsulation.

DETAILED DESCRIPTION OF THE INVENTION

This invention also includes a method for producing the formulations disclosed herein. The process comprises the steps of:

a) combining, preferably with mixing or stirring, the PEG and surfactant components to create a first carrier mixture;

b) raising the temperature of the first carrier mixture to a range of from about 75° C. to about 95° C., preferably from about 80° C. to about 90° C.;

c) adding the active pharmacological agent (VPA-985) to create a first pharmaceutical composition mixture;

d) stirring the first pharmaceutical composition mixture, preferably with heating, until the first pharmaceutical composition mixture is clear, preferably at a temperature from about 115° C. to about 170° C., preferably from about 130° C. to about 170° C., more preferably at a temperature from about 135° C. to about 150° C.;

e) cooling the first pharmaceutical composition, if necessary, to a temperature of from about 60° C. to about 110° C., preferably from about 80° C. to about 90° C.;

f) adding the amount of sucrose fatty acid ester(s) and/or povidone to create a final pharmaceutical composition mixture, preferably with stirring until the final pharmaceutical composition mixture is clear.

In cases wherein optional antioxidants or preservatives are used, such as BHA, BHT, etc., the following steps may be employed:

a) combining, preferably with mixing or stirring, the PEG component (such as a mixture of PEG 400 and PEG 1000) and the surfactant component (such as Polysorbate 80) to create a first carrier mixture;

b) raising the temperature of the first carrier mixture to a range of from about 75° C. to about 95° C., preferably from about 80° C. to about 90° C.;

c) adding to the first carrier mixture optional antioxidant or preservative components to create a second carrier mixture, which is then stirred or otherwise mixed until the second carrier mixture is a clear solution;

d) adding the active pharmacological agent or drug, component (VPA-985) to create a first pharmaceutical composition mixture;

e) stirring the first pharmaceutical composition mixture, preferably with heating, until the first pharmaceutical composition mixture is clear, preferably at a temperature from about 130° C. to about 150° C., more preferably at a temperature from about 135° C. to about 145° C.;

f) optionally cooling the first pharmaceutical composition to a temperature of from about 75° C. to about 95° C., preferably from about 80° C. to about 90° C.;

g) adding the amount of sucrose fatty acid ester(s) and/or povidone to create a final pharmaceutical composition mixture, preferably with stirring until the final pharmaceutical composition mixture is clear.

One skilled in the art will understand the viscosity and form of the final formulation may be manipulated with components within the scope of this invention and temperature ranges during processing. For instance, a fluid or semi-solid composition may be produced with the more fluid PEG, surfactant and PVP species within the scope of this invention. More gel-like, viscous or semi-solid compositions may be produced with combinations of higher molecular weight PEG components and PVP components having higher K values. Moreover, the components may be cooled below their melting point if milling or other processing of the final composition is desired. To create a more pelletized initial composition, a fluid composition of this invention may be sprayed onto a cooled Teflon®-coated surface to form small solid spheres, which may be individually coated or collected for further processing.

Specific non-limiting examples of formulations within the scope of this invention are provided below.

EXAMPLE 1
50 mg/capsule: VPA-985 Oral Formulation at 10% Drug Loading

In place of the polysorbate 80 in this formulation of Example 1, other polysorbate series such as Tween 20, 40 and 60 can also be used, alone or in combination with each other and/or polysorbate 80.

|  | (% w/w) | per capsule (mg) | 20,000 capsule batch (g) |
|---|---|---|---|
| Active Ingredient: | | | |
| VPA-985 @ 100% | 10.42 | 50.00 | 1000.00 |
| Inactive Ingredients: | | | |
| PEG 1000, NF | 30.96 | 148.61 | 2,972.16 |
| Povidone USP K-17 | 10.00 | 48.00 | 960.00 |
| Polysorbate 80, NF | 10.00 | 48.00 | 960.00 |
| BHT, NF | 0.09 | 0.42 | 8.32 |
| BHA, NF | 0.87 | 4.16 | 83.2 |
| PBG 400, NF[2] | Q.S. to 100 | Q.S. to 480.00 | Q.S. to 9,600 |

1. Weigh the Polysorbate 80, PEG 400, and PEG 1000 into a suitable mixing vessel, stir using a top mounted mixer, and warm to 85±5° C.

2. Add BHT and BHA to the mixing vessel, very slowly to prevent formation of lumps. Continue stirring at 85±5° C., until a clear solution was formed.

3. Add VPA-985 to the vessel at 85±5° C., very slowly to prevent formation of lumps. Slowly raise the temperature to 125±5° C., and stir until VPA-985 dissolves completely.

4. Cool the solution in step 4. to 60±5° C.

5. Add Povidone, USP, K-17 (Plasdone C-15, ISP) slowly to step 5, to prevent the formation of lumps.

Let the solution warm up to 85±5° C. Stir until the solution becomes clear.

6. Encapsulate 480 mg of the finished solution (in step 10) into size 1 capsules at 38±5° C. using either soft or hard gelatin capsule filler. During encapsulation cool the body of capsule using cool Nitrogen to prevent leaking.

7. Band seal the capsules with gelatin solution (optional).

EXAMPLE 2
50 mg/capsule: VPA-985 Oral Formulation at 10% Drug Loading

In place of surfactant used in this formulation (poloxamer 188), other polymers in the series such as Pluronic L44, Pluronic L101 can also be used.

|  | (% w/w) | per capsule (mg) | 20,000 capsule batch (g) |
|---|---|---|---|
| Active Ingredient: | | | |
| VPA-985 @ 100% | 10.42 | 50.00 | 1000.00 |
| Inactive Ingredients: | | | |
| Povidone USP K-17 (Plasdone C-15, ISP) | 10.00 | 48.00 | 960.00 |
| Poloxamer 188, NF | 12.00 | 57.60 | 1152.00 |
| BHT NF | 0.09 | 0.42 | 8.32 |
| BHA NF | 0.87 | 4.16 | 83.20 |
| PEG 400 NF | Q.S. to 100 | Q.S. to 480.00 | Q.S. to 9600 g |

This formulation is manufactured the same as that of the formula of Example 1 (50 mg/capsule) with the exception that 12% of poloxamer was used in place of the polysorbate 80 in this formulation. The encapsulation weight is 480 mg.

EXAMPLE 3
50 mg/capsule

Example 4 provides a formulation with a combination of two or more surfactants.

|  | (% w/w) | per capsule (mg) | 20,000 capsule batch (g) |
|---|---|---|---|
| Active Ingredient: | | | |
| VPA-985 @ 100% | 10.64 | 51.07 | 1,021.44 |
| Inactive Ingredient: | | | |
| PEG 1000, NF | 28.60 | 137.28 | 2,745.60 |
| Povidone USP K-17 (Plasdone C-15, ISP) | 10.00 | 48.00 | 960.00 |
| Polysorbate 40, NF | 5.00 | 24.00 | 480.00 |
| Poloxamer 188, NF | 10.00 | 48.00 | |
| BHT, NF | 0.09 | 0.43 | 8.64 |
| BHA, NF | 0.87 | 4.18 | 83.52 |
| PEG 400, NF | Q.S. to 100 | Q.S. to 480.00 | Q.S.to 9600.00 |

The formulation of Example 3 is manufactured the same as that of Example 1 (50 mg/capsule) with the exception that two surfactants, polysorbate 40 and poloxamer 188 were added in step 1 along with PEG 400 and PEG 1000. The encapsulation weight is 480 mg.

EXAMPLE 4

25 mg/capsule: VPA-985 Oral Formulation at 5% Drug Loading

|  | (% w/w) | per capsule (mg) | 20,000 capsule batch (g) |
|---|---|---|---|
| Active Ingredient: |  |  |  |
| VPA-985 @ 100% | 5.49 | 25.00 | 500.00 |
| Inactive Ingredient: |  |  |  |
| PEG 1000, NF | 32.66 | 148.61 | 2,972.16 |
| Povidone, USP K-17 (Plasdone C-15, ISP) | 10.55 | 48.00 | 960.00 |
| Polysorbate 80, NF | 10.55 | 48.00 | 960.00 |
| BHT, NF | 0.09 | 0.42 | 8.32 |
| BHA, NF | 0.91 | 4.16 | 83.2 |
| PEG 400, NF[2] | Q.S. to 100 | Q.S. to 455.00 | Q.S. to 9,100 g |

The formulation of Example 4 is produced in the same manner as that of 50 mg/capsule, above, with the exception that the heating temperature to solubilize VPA-985 in step 3 is 115±5° C., instead of 120±5° C. The encapsulation weight is 455 mg.

EXAMPLE 5

100 mg/capsule: VPA-985 Oral Formulation at 15% Drug Loading

|  | (% w/w) | per capsule (mg) | 20,000 capsule batch (g) |
|---|---|---|---|
| Active Ingredient: |  |  |  |
| VPA-985 @ 100% | 15.38 | 100.00 | 2,000.00 |
| Inactive Ingredient: |  |  |  |
| PEG 1000, NF | 28.98 | 188.35 | 3,767.05 |
| Povidone USP K-17 (Plasdone C-15, ISP)[3] | 10.00 | 65.00 | 1,300.00 |
| Polysorbate 80, NF | 9.45 | 61.39 | 1,227.91 |
| BHT, NF | 0.08 | 0.53 | 10.64 |
| BHA, NF | 0.82 | 5.32 | 106.42 |
| PEG 400, NF | Q.S. to 100 | Q.S. to 650.00 | Q.S. to 13,000.00 |

This formulation is produced with the same steps as the 50 mg/capsule, above, with the exception that the heating temperature to solubilize VPA-985 in step 3 is 145±5° C., instead of 120±5° C. The encapsulation weight is 650 mg in size 0 hard gelatin capsule.

EXAMPLE 6

VPA-985: 150 mg in Size 00 Capsule

|  | (% w/w) | per capsule (mg) | 20,000 capsule batch (g) |
|---|---|---|---|
| Active Ingredient: |  |  |  |
| VPA-985 @ 100% | 16.48 | 149.97 | 2,999.36 |
| Inactive Ingredients: |  |  |  |
| PEG 1000, NF | 26.3 | 239.33 | 4,786.60 |
| Povidone USP K-17 (Plasdone C-15, ISP) | 15 | 136.50 | 2,730.00 |
| Polysorbate 80, NF | 9.32 | 84.81 | 1,696.24 |
| BHT, NF | 0.08 | 0.73 | 14.56 |
| BHA, NF | 0.81 | 7.37 | 147.42 |
| PEG 400, NF | Q.S. to 100 | Q.S. to 910.00 | Q.S. to 18,200.00 |

This formulation of Example 6 is produced with the same steps as that of 50 mg/capsule with the exception of the heating temperature to solubilize VPA-985 in step 3 is 150±5° C., instead of 145±5° C. The encapsulation weight is 910 mg in size 00 hard gelatin capsule.

The following specific Examples 7 through 11 shown in Table 1, below, were N-[4-(5H-pyrrolo[2,1-c][1,4]benzodiazepin-10(11H)ylcarbonyl)-3-chlorophenyl]-5-fluoro-2-methyl-benzamide (VPA-985) with varying concentrations of PEG 400, PEG 1000, two PVP components with respective K values of 15 and 90, and a combination of BHA and BHT as an adjuvant component.

TABLE 1

| Example No. | PEG 400 (%) | PEG 1000 (%) | PVP K15 (%) | PVP K90 (%) | BHT (%) | BHA (%) | NATC (%) | VPA-985 (%) |
|---|---|---|---|---|---|---|---|---|
| 7 | 55.40 | 20.00 | 10.00 | 0.00 | 0.20 | 2.00 | 2.40 | 10.00 |
| 8 | 40.40 | 35.00 | 10.00 | 0.00 | 0.20 | 2.00 | 2.40 | 10.00 |
| 9 | 75.40 | 0.00 | 5.00 | 5.00 | 0.20 | 2.00 | 2.40 | 10.00 |
| 10 | 65.40 | 10.00 | 0.00 | 10.00 | 0.20 | 2.00 | 2.40 | 10.00 |
| 11 | 40.40 | 35.00 | 5.00 | 5.00 | 0.20 | 2.00 | 2.40 | 10.00 |

Similarly, the following Examples 12 trough 32 were formulated by the methods herein using PEG 400, PEG 1000, PVP with a K value of 17, VPA-985, BHA and BHT as antioxidants or preservatives and the additional components listed as "other".

TABLE 2

| Ex. No. | PEG 400 | PEG 1000 | PVP K-17 | VPA-985 | BHA | BHT | Other | Other |
|---|---|---|---|---|---|---|---|---|
| 12 | 40.40 | 35.00 | 10.00 | 10.00 | 2.00 | 0.20 | Sodium Taurocholate 2.40 | — |
| 13 | 75.40 | — | 5.00 | 10.21 | 2.00 | 0.20 | Sodium Taurocholate 2.40 | PVP K-90 5.00 |
| 14 | 42.59 | 35.00 | 10.00 | 10.21 | 2.00 | 0.20 | — | — |

TABLE 2-continued

| Ex. No. | PEG 400 | PEG 1000 | PVP K-17 | VPA-985 | BHA | BHT | Other | Other |
|---|---|---|---|---|---|---|---|---|
| 15 | 34.35 | 28.23 | 10.00 | 10.21 | 2.00 | 0.20 | Poloxamer 188 15.00 | — |
| 16 | 42.59 | 20.00 | 10.00 | 10.21 | 2.00 | 0.20 | Poloxamer 188 15.00 | — |
| 17 | 37.10 | 30.49 | 10.00 | 10.21 | 2.00 | 0.20 | Poloxamer 188 10.00 | — |
| 18 | 35.72 | 29.36 | 10.00 | 10.21 | 2.00 | 0.20 | Poloxamer 188 12.50 | — |
| 19 | 34.35 | 28.23 | 10.00 | 10.21 | 2.00 | 0.20 | Poloxamer 188 15.00 | — |
| 20 | 37.10 | 30.49 | 10.00 | 10.21 | 2.00 | 0.20 | Poloxamer 188 10.00 | — |
| 21 | 34.35 | 28.23 | 10.00 | 10.21 | 2.00 | 0.20 | Poloxamer 188 15.00 | — |
| 22 | 35.72 | 29.36 | 10.00 | 10.21 | 2.00 | 0.20 | Poloxamer 188 12.50 | — |
| 23 | 36.86 | 30.30 | 10.00 | 10.64 | 2.00 | 0.20 | Pluronic L44 10.00 | — |
| 24 | 36.86 | 30.30 | 10.00 | 10.64 | 2.00 | 0.20 | Pluronic L101 10.00 | — |
| 25 | 39.61 | 32.55 | 10.00 | 10.64 | 2.00 | 0.20 | Tween 40 5.00 | — |
| 26 | 41.25 | 33.91 | 10.00 | 10.64 | 2.00 | 0.20 | Tween 40 2.00 | — |
| 27 | 39.61 | 32.55 | 10.00 | 10.64 | 2.00 | 0.20 | Tween 20 5.00 | — |
| 28 | 41.25 | 33.91 | 10.00 | 10.64 | 2.00 | 0.20 | Tween 20 2.00 | — |
| 29 | 34.12 | 28.04 | 10.00 | 10.64 | 2.00 | 0.20 | Tween 40 5.00 | Poloxamer 188 10.00 |
| 30 | 36.86 | 30.30 | 10.00 | 10.64 | 2.00 | 0.20 | Tween 40 | — |
| 31 | 36.86 | 30.30 | 10.00 | 10.64 | 2.00 | 0.20 | Tween 80 10.00 | — |
| 32 | 34.12 | 28.04 | 10.00 | 10.64 | 2.00 | 0.20 | Tween 80 5.00 | Poloxamer 188 10.00 |

EXAMPLE 33

25 capsule in Size #3 capsule: Oral formulation at 10% Drug Loading

In place of the polysorbate 80, other polysorbate series such as Tween 20, 40 and 60 can also be used.

|  | (% w/w) | per capsule (mg) | 20,000 capsule batch (g) |
|---|---|---|---|
| Active Ingredient: |  |  |  |
| VPA-985 @ 100% | 10.42 | 25 | 500.00 |
| Inactive Ingredients: |  |  |  |
| PEG 1000, NF | 30.96 | 74.31 | 1,486.08 |
| Povidone USP K-17 | 10.00 | 24.00 | 480.00 |
| Polysorbate 80, NF | 10.00 | 24.00 | 480.00 |
| BHT, NF | 0.09 | 0.21 | 4.16 |
| BHA, NF | 0.87 | 2.08 | 41.6 |
| PEG 400, NF[2] | Q.S. to 100 | Q.S. to 240 | Q.S. to 4800 |

What is claimed:

1. A pharmaceutical composition comprising:
   a) from about 1% to about 20% of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof;
   b) from about 1% to about 18% of a surfactant component;
   c) from about 50% to about 80% of a component of one or more polyethylene glycols; and
   d) from about 1% to about 20% of a component of:
      i) one or more sucrose fatty acid esters; or
      ii) a polyvinylpyrrolidone with a K value between about 15 and 90; or
      iii) a combination of one or more sucrose fatty acid esters and polyvinylpyrrolidone.

2. A pharmaceutical composition of claim 1 comprising:
   a) from about 5% to about 16% of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof;
   b) from about 5% to about 15% of a surfactant component;
   c) from about 55% to about 70% of a component of one or more polyethylene glycols; and
   d) from about 1% to about 20% of a component of:
      i) one or more sucrose fatty acid esters; or
      ii) a polyvinylpyrrolidone with a K value between about 15 and 90; or
      iii) a combination of one or more sucrose fatty acid esters and polyvinylpyrrolidone, as defined above.

3. A pharmaceutical composition of claim 1 wherein the surfactant component comprises polysorbate 20, polysorbate 60, polysorbate 40, polysorbate 80, Span 80 Sorbitan Oleate, polysorbate 81, polysorbate 85, polysorbate 120, sodium taurocholates, sodium deoxytaurocholates, chenodeoxycholic acid, ursodeoxycholic acid, pluronic or poloxamers, or combinations thereof.

4. A pharmaceutical composition of claim 1 wherein the component of one or more polyethylene glycols comprises one or more polyethylene glycols having an average molecular weight between about 190 to about 3450.

5. A pharmaceutical composition of claim 4 wherein the component of one or more polyethylene glycols comprises one or more polyethylene glycols having an average molecular weight between about 400 and 1540.

6. A pharmaceutical composition of claim 4 wherein the component of one or more polyethylene glycols comprises a mixture of PEG 400 and PEG 1000 in a ratio of between about 2.5:1 to about 1:2.5.

7. A pharmaceutical composition of claim 1 wherein the polyvinylpyrrolidone component has a K value of about 17.

8. A pharmaceutical composition comprising:
   a) from about 1% to about 20% of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof;
   b) from about 5% to about 18% of a surfactant component;
   c) from about 50% to about 80% of a component of one or more polyethylene glycols;
   d) from about 1% to about 20% of one or more sucrose fatty acid esters or polyvinylpyrrolidone with a K value between about 15 and 90; and
   e) from about 0.1% to about 3% of one or more antioxidants or preservatives.

9. A pharmaceutical composition of claim 8 wherein:
   a) the surfactant component comprises polysorbate 20, polysorbate 60, polysorbate 40, polysorbate 80, Span 80 Sorbitan Oleate, polysorbate 81, polysorbate 85, polysorbate 120, sodium taurocholates, sodium deoxytaurocholates, chenodeoxycholic acid, ursodeoxycholic acid, pluronic or poloxamers, or combinations thereof;
   b) the component of one or more polyethylene glycols comprises one or more polyethylene glycols having an average molecular weight between about 400 and 1540; and
   c) the one or more antioxidants or preservatives are selected from ascorbyl palmitate, benzyl alcohol, butylated hydroxyanisole, or butylated hydroxytoluene, or combinations thereof.

10. A pharmaceutical composition of claim 8 comprising:
    a) from about 5% to about 16% of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof;
    b) from about 5% to about 15% of a surfactant component;
    c) from about 55% to about 70% of a component of one or more polyethylene glycols;
    d) from about 1% to about 20% of one or more sucrose fatty acid esters or polyvinylpyrrolidone with a K value between about 15 and 90;
    e) from about 0.3% to about 2.5% (% w/w) BHA and/or from about 0.005% to about 0.15% (% w/w) BHT.

11. A pharmaceutical composition of claim 8 comprising:
    a) from about 5% to about 16% of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof;
    b) from about 5% to about 15% of a surfactant component comprising polysorbate 20, polysorbate 60, polysorbate 40, polysorbate 80, Span 80 Sorbitan Oleate, polysorbate 81, polysorbate 85, polysorbate 120, sodium taurocholates, sodium deoxytaurocholates, chenodeoxycholic acid, ursodeoxycholic acid, ursodeoxycholic acid, pluronic or poloxamers, or combinations thereof;
    c) a component of from about 55% to about 70% of one or more polyethylene glycols having an average molecular weight between about 400 and 1540;
    d) from about 1% to about 20% of polyvinylpyrrolidone (PVP) with a K value between about 15 and 90; and
    e) from about 0.3% to about 2.5% (% w/w) BHA and from about 0.005% to about 0.15% (% w/w) BHT.

12. A pharmaceutical composition of claim 1 which is contained within a hard or soft gelatin capsule.

13. A process from formulating a pharmaceutical composition which comprises from about 1% to about 20% of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof; from about 1% to about 18% of a surfactant component; from about 50% to about 80% of a component of one or more polyethylene glycols; and from about 1% to about 20% of a component of one or more sucrose fatty acid esters or a polyvinylpyrrolidone with a K value between about 15 and 90; or a combination of one or more sucrose fatty acid esters and polyvinylpyrrolidone; the process comprising the steps of:
    a) combining the surfactant component and the component of one or more polyethylene glycols to create a first carrier mixture;
    b) raising the temperature of the first carrier mixture to a range of from about 75° C. to about 95° C.;
    c) adding the N-[4-(5H-pyrrolo[2,1-c][1,4]benzodiazepin-10(11H)yl-carbonyl)-3-chlorophenyl]-5-fluoro-2-methylbenzamide, or a pharmaceutically acceptable salt thereof, to create a first pharmaceutical composition mixture;
    d) raising the temperature of the first pharmaceutical composition to a temperature from about 115° C. to about 170° C. and mixing or stirring until the first pharmaceutical composition mixture is clear;
    e) cooling the first pharmaceutical composition to a temperature of from about 75° C. to about 95° C.;
    g) adding the amount of one or more sucrose fatty acid esters and/or povidone to create a final pharmaceutical composition mixture.

14. A process of claim 13 comprising the steps:
    a) combining the surfactant component and the component of one or more polyethylene glycols to create a first carrier mixture;
    b) raising the temperature of the first carrier mixture to a range of from about 80° C. to about 90° C.;
    c) adding the N-[4-(5H-pyrrolo[2,1-c][1,4]benzodiazepin-10(11H)yl-carbonyl)-3-chlorophenyl]-5-fluoro-2-methylbenzamide, or a pharmaceutically acceptable salt thereof, to create a first pharmaceutical composition mixture;
    d) raising the temperature of the first pharmaceutical composition to a temperature from about 135° C. to about 145° C. and mixing or stirring until the first pharmaceutical composition mixture is clear;
    e) cooling the first pharmaceutical composition, if necessary, to a temperature of from about 80° C. to about 90° C.;
    g) adding the amount of sucrose fatty acid ester(s) and/or povidone to create a final pharmaceutical composition mixture.

15. A process for formulating a pharmaceutical composition comprising from about 1% to about 20% of N-[4-

(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof; from about 5% to about 18% of a surfactant component; from about 50% to about 80% of a component of one or more polyethylene glycols; a component of from about 1% to about 20% of one or more sucrose fatty acid esters or polyvinylpyrrolidone with a K value between about 15 and 90; and from about 0.1% to about 3% of one or more adjuvants; the process comprising the steps of:

a) combining the component of one or more polyethylene glycols and the surfactant component to create a first carrier mixture;

b) raising the temperature of the first carrier mixture to a range of from about 75° C. to about 95° C.;

c) adding to the first carrier mixture the one or more antioxidants or preservatives to create a second carrier mixture;

d) adding the N-[4-(5H-pyrrolo[2,1-c][1,4]benzodiazepin-10(11H)yl-carbonyl)-3-chlorophenyl]-5-fluoro-2-methylbenzamide, or a pharmaceutically acceptable salt thereof, to create a first pharmaceutical composition mixture;

e) raising the first pharmaceutical composition mixture to a temperature from about 130° C. to about 150° C., with stirring or mixing;

f) cooling the first pharmaceutical composition to a temperature of from about 75° C. to about 95° C.;

g) adding the component of from about 1% to about 20% of one or more sucrose fatty acid esters or polyvinylpyrrolidone with a K value between about 15 and 90 to create a final pharmaceutical composition mixture.

16. The process of claim 15 wherein:

a) the surfactant component comprises polysorbate 20, polysorbate 60, polysorbate 40, polysorbate 80, Span 80 Sorbitan Oleate, polysorbate 81, polysorbate 85, polysorbate 120, sodium taurocholates, sodium deoxytaurocholates, chenodeoxycholic acid, ursodeoxycholic acid, pluronic or poloxamers, or combinations thereof;

b) the component of one or more polyethylene glycols comprises one or more polyethylene glycols having an average molecular weight between about 400 and 1540; and c) the one or more antioxidants or preservatives are selected from ascorbic palmitate, benzyl alcohol, butylated hydroxyanisole, or butylated hydroxytoluene, or combinations thereof.

17. A process for formulating a pharmaceutical composition comprising from about 1% to about 20% of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof; from about 5% to about 18% of a surfactant component; from about 50% to about 80% of a component of one or more polyethylene glycols; a component of from about 1% to about 20% of polyvinylpyrrolidone with a K value between about 15 and 90; and an antioxidant or preservative component of from about 0.3% to about 2.5% butylated hydroxyanisole and from about 0.005% to about 0.15% butylated hydroxytoluene; the process comprising the steps of:

a) combining, preferably with mixing or stirring, the component of one or more polyethylene glycols and the surfactant component to create a first carrier mixture;

b) raising the temperature of the first carrier mixture to a range of from about 75° C. to about 95° C.;

c) adding to the first carrier mixture the antioxidant or preservative component to create a second carrier mixture;

d) adding the N-[4-(5H-pyrrolo[2,1-c][1,4]benzodiazepin-10(11H)yl-carbonyl)-3-chlorophenyl]-5-fluoro-2-methylbenzamide, or a pharmaceutically acceptable salt thereof to create a first pharmaceutical composition mixture;

e) raising the temperature of the first pharmaceutical composition mixture to a temperature from about 130° C. to about 150° C.;

f) stirring or mixing the first pharmaceutical composition mixture until the first pharmaceutical composition mixture is clear;

f) bringing the first pharmaceutical composition to a temperature of from about 75° C. to about 95° C.;

g) adding the component of from about 1% to about 20% of povidone to create a final pharmaceutical composition mixture.

18. The process of claim 17 wherein:

a) the surfactant component comprises polysorbate 20, polysorbate 60, polysorbate 40, polysorbate 80, Span 80 Sorbitan Oleate, polysorbate 81, polysorbate 85, polysorbate 120, sodium taurocholates, sodium deoxytaurocholates, chenodeoxycholic acid, ursodeoxycholic acid, pluronic or poloxamers, or combinations thereof; and b) the component of one or more polyethylene glycols comprises one or more polyethylene glycols having an average molecular weight between about 400 and 1540.

19. A process for formulating a pharmaceutical composition comprising from about 5% to about 16% of N-[4-(5H-pyrrolo[2,1-c[]1,4]benzodiazepin-10(11H)ylcarbonyl)-3-chlorophenyl]-5-fluoro-2-methylbenzamide, or a pharmaceutically acceptable salt thereof; from about 5% to about 15% of a surfactant component; from about 55% to about 70% of a component of one or more polyethylene glycols; a component of from about 5% to about 15% of polyvinylpyrrolidone with a K value between about 15 and 90; and an antioxidant or preservative component of from about 0.3% to about 2.5% butylated hydroxyanisole and from about 0.005% to about 0.15% butylated hydroxytoluene; the process comprising the steps of:

a) combining, preferably with mixing or stirring, the component of one or more polyethylene glycols and the surfactant component to create a first carrier mixture;

b) raising the temperature of the first carrier mixture to a range of from about 80° C. to about 90° C.;

c) adding to the first carrier mixture the antioxidant or preservative component to create a second carrier mixture;

d) adding the N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof to create a first pharmaceutical composition mixture;

e) raising the temperature of the first pharmaceutical composition mixture to a temperature from about 135° C. to about 145° C.;

f) stirring or mixing the first pharmaceutical composition mixture until the first pharmaceutical composition mixture is clear;

f) bringing the first pharmaceutical composition to a temperature of from about 80° C. to about 90° C.;

g) adding the component of from about 5% to about 15% of povidone to create a final pharmaceutical composition mixture.

* * * * *